United States Patent [19]

Troutner et al.

[11] 4,067,323
[45] Jan. 10, 1978

[54] LIGHT FOR VAGINAL SPECULUM

[75] Inventors: Vernon H. Troutner, St. Petersburg; Raymond W. Simmons, North Pinellas Park, both of Fla.

[73] Assignee: Concept Inc., Clearwater, Fla.

[21] Appl. No.: 636,833

[22] Filed: Dec. 2, 1975

[51] Int. Cl.² .............................................. A61B 1/06
[52] U.S. Cl. ...................... 128/18; 128/23; 362/109
[58] Field of Search ............... 128/11, 13, 16, 17, 128/18, 22, 23, 132 R, 132 D; 240/2 MA, 2 R, 2 L, 26, 2.18, 41.5, 6.4 B, 6.4 R, 2 E, 6.46; 150/52 R; 206/45.33

[56] References Cited
U.S. PATENT DOCUMENTS

| | | | |
|---|---|---|---|
| 2,320,709 | 6/1943 | Arnesen | 128/17 |
| 2,879,381 | 3/1959 | Coffey | 240/26 |
| 3,789,835 | 2/1974 | Whitman | 128/18 |
| 3,794,091 | 2/1974 | Ersek et al. | 150/52 R |
| 3,890,961 | 6/1975 | Moore et al. | 128/17 |

OTHER PUBLICATIONS

Catalog, Welch Allyn Inc., Skaneateles Falls, NY, 13153, pp. 27 and 28, Aug. 1974.

Primary Examiner—Robert W. Michell
Assistant Examiner—Henry S. Layton
Attorney, Agent, or Firm—Gipple & Hale

[57] ABSTRACT

A portable light for a vaginal speculum of the type having a body and a plurality of dilator members extending from the body. The light comprises a casing which defines a curved end wall and a boss which houses a light bulb. Batteries are mounted in the casing and are electrically connected to the bulb by a switch which is moveably mounted on the casing. A flexible bag is placed around the casing and the casing and bag are mounted on the speculum body by engaging the boss and curved end wall in frictional engagement with the speculum body.

5 Claims, 15 Drawing Figures

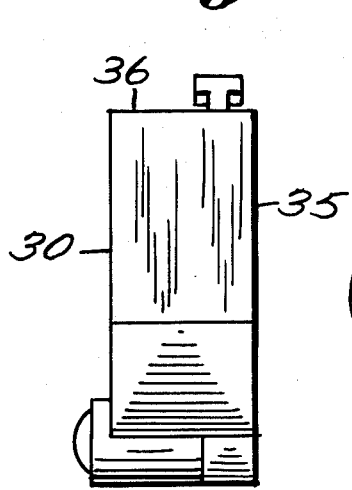
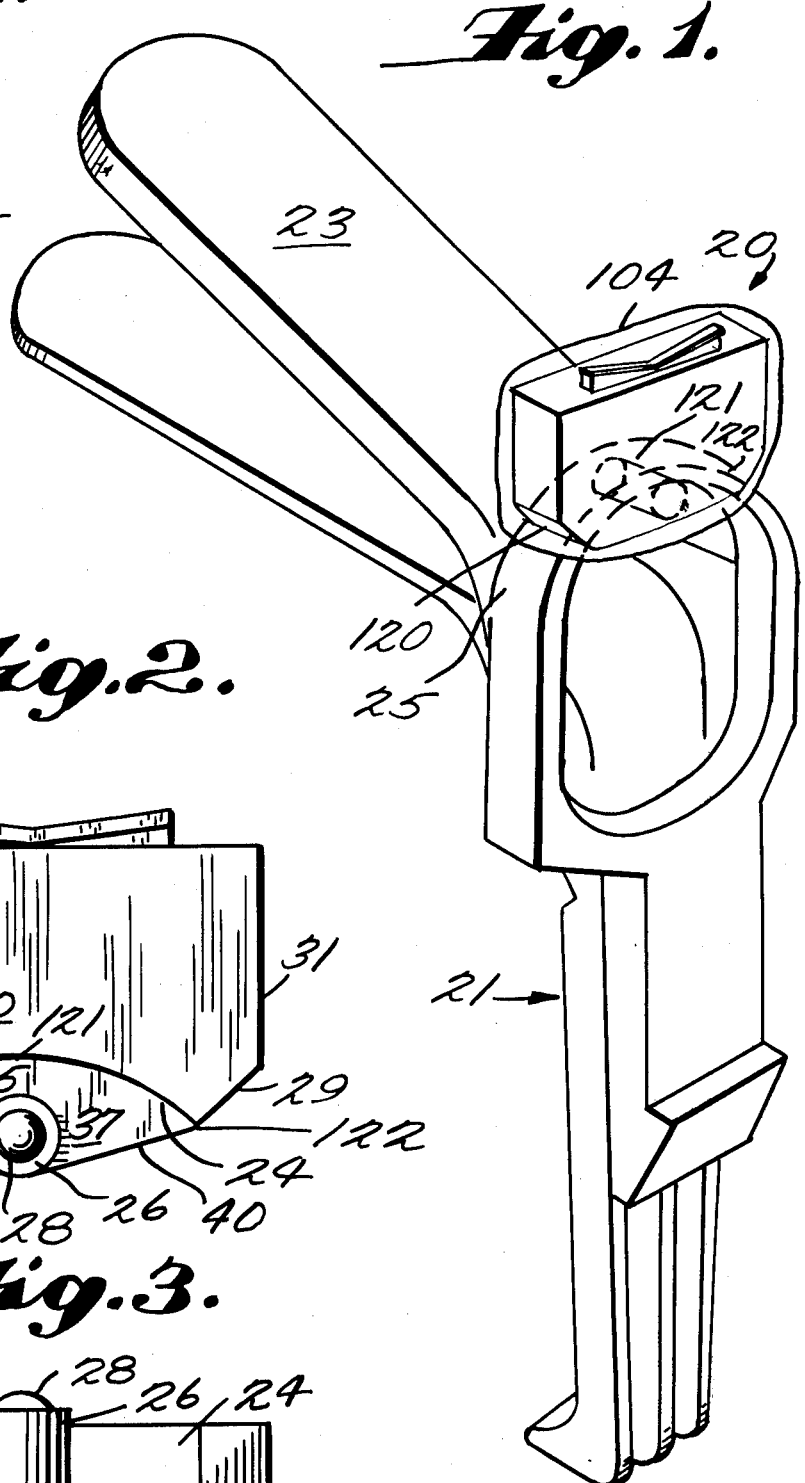
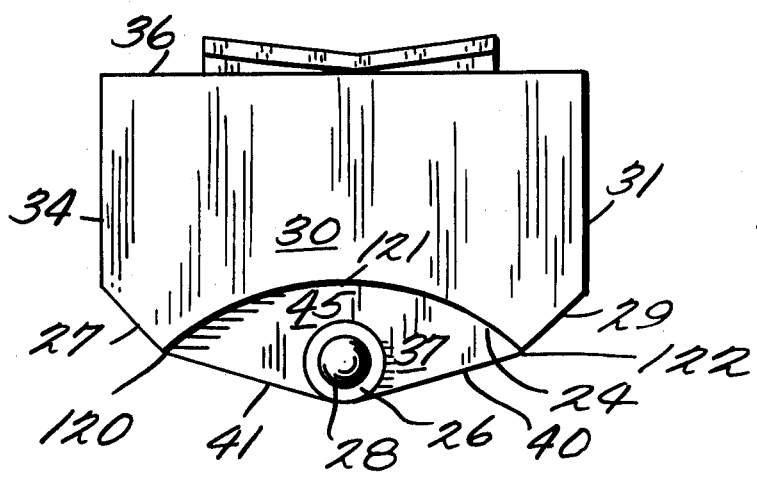
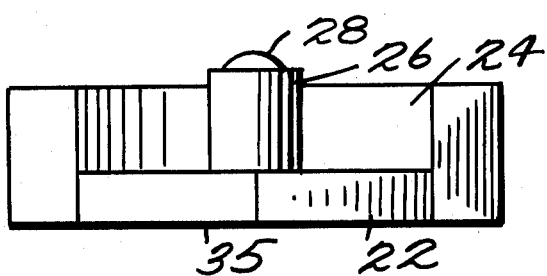

LIGHT FOR VAGINAL SPECULUM

BACKGROUND OF THE INVENTION

The present invention generally pertains to surgical lights and more particularly to a light for vaginal speculums.

In the examination and treatment of interior body cavities it is usually necessary to employ an instrument to dilate the body cavities. Speculums of various kinds have been devised for this purpose.

Generally speculums which are used are of a type which permit rotary or arcuate relative movement of the blades. In such speculums, a pivotal or hinged connection is provided between the blades. As the blades are moved relative to one another they describe an arcuate path about a transverse axis passing through the pivotal connection.

Other speculums such as the one shown in U.S. Pat. No. 3,246,646 are constructed to permit relative angular rotation as well as bodily separation of the blades.

Regardless of which kind of speculum is used in the surgical examination or usage it is necessary to provide a source of light into the body cavity so that the same can be examined or acted upon. Previous means of providing such illumination have been for a physician to hold a light in one hand and try to illuminate the interior cavity or to reflect light from some exterior source off of a reflector placed on the head or on some portion of the physician's body into the body cavity. The present invention provides a portable light which is adapted to be removably placed onto a variety of speculum instruments so that illumination can be directed into the body cavity when the speculum blades are separated to expand the entrance orifice. In addition, the light is novelly placed in a thin plastic bag so that the light is sanitary during use and can be reused on additional speculums for other examinations. This use of a throw away transparent plastic covering or bag over-comes the difficulty involved in the sterilization or cleaning of previously used light sources resulting in battery destruction or in the use of cumbersome light devices. Furthermore, the small size of the light casing and easy adaptability of fastening the casing onto the speculum instrument allows for aligned easy illumination of the body cavity without unduly incumbering the physician.

The above mentioned purposes are more readily apparent when read in conjunction with the following detailed description of the preferred embodiment of the present invention.

BRIEF DESCRIPTION OF THE DRAWINGS

FIG. 1 is a perspective view of the light mounted on the vaginal speculum enclosed by a transparent bag;

FIG. 2 is an enlarged front elevational view of the light shown in FIG. 1;

FIG. 3 is an enlarged bottom plan view of the light shown in FIG. 1;

FIG. 4 is an enlarged side elevational view of the light shown in FIG. 1;

DETAILED DESCRIPTION OF THE DRAWINGS

Figure 5:
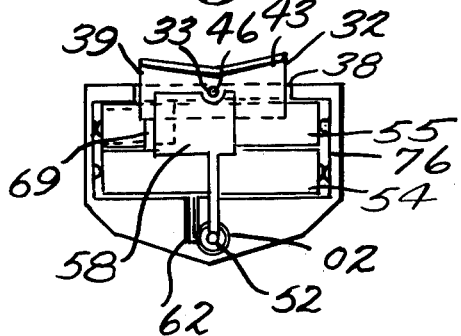
FIG. 5 is a rear view of the light shown in FIG. 1 with the back plate removed.
Figure 6:
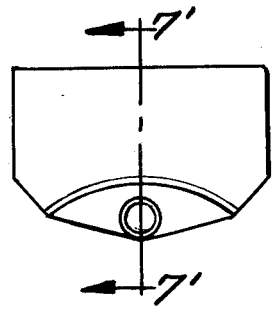
FIG. 6 is a front elevational view of the light shown in FIG. 5.

The inventive light 20 and its components as shown by the drawings frictionally engages and is held upon the upper curvature 25 of the vaginal speculum 21 as is shown in FIG. 1.

The light 20 has a generally planar configured casing formed with an angular base 22 and two sets of parallel sides 30, 35 and 31, 34 which perpendicularly intersect the top 36 of the casing. Slanted walls 29 and 27 are formed on the casing so that their lower ends intersect angular base 22 and their upper ends intersect sides 31 and 34. The lower ends of the slanted walls form the ends of a curved end wall 24 cut into side 30. The curved end wall 24 extends around a hollow protuberance 26 in the form of a boss extending from planar surface 37. The boss 26 serves as a bulb holder. Walls 40 and 41 of base 22 meet at a point which is beneath the bulb holder. The bulb holder 26 is substantially perpendicular to surface 37 and projects outwardly from the planar surface. A light bulb 28 is placed within and supported by the bulb holder. The light is designed so that the upper curvature 25 of the vaginal speculum body is adapted to fit within the space or channel 45 formed between the curved wall 24 and the outer surface of boss 26.

The closest space between boss 26 and wall 24 is about equal to the thickness of the upper curvature 25 of the speculum. The radius of curvature of wall 24 is less than the radius of the upper curvature 25 of the speculum. Consequently it can be seen that the light 20 when placed upon the vaginal speculum 21 is frictionally engaged by the speculum body at three points, 120, 121, and 122 and held in place. The protuberance 26 may also be constructed with a frustro-conical configuration or in any other suitable configuration and the end wall in a linear or angular configuration so that the resulting space between the two will be adapted to fit on the speculum in a firm positon. The bulb 28 when in position on the speculum holding protuberance is adapted to direct light down along the area formed between the speculum cavity separation blades 23 so that the dilated body cavity will be illuminated.

The top 36 of the casing is provided with a cut-out recess 38 in which is mounted a pivoted switch 32. The pivoted switch is formed with two wings 39 and 43 and rotates about a pivot pin 46 formed in the casing.

Figure 7:
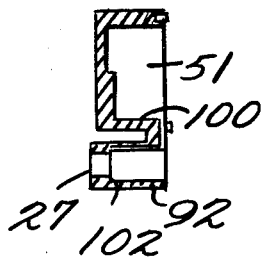
FIG. 7 is a cross sectional view of the casing of the light of FIG. 6 taken along lines 7'—7'.
Figure 9:
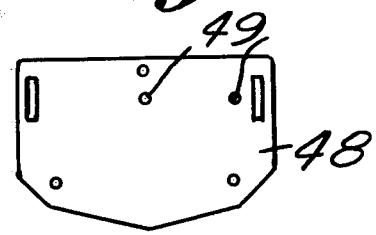
FIG. 9 is a rear elevational view of the back plate of the light.

A cover plate 48 is mounted on the casing. The cover plate has the same configuration as the rear portion of the casing. The cover plate 48 as shown in FIG. 9 fits over the entire rear perimeter of the casing and encloses the batteries and electrical contacts. The interior of the casing forms a battery cavity 51, as shown in FIG. 7.

The battery cavity holds two ordinary batteries 54 and 55 which serve as the power source for the light. At the rear of light bulb 28 is a light bulb contact 52.

Figure 15:
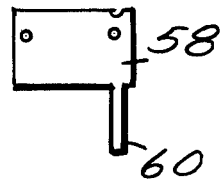
FIG. 15 is a plan view of the switch plate conductor of the light.

A switch plate conductor 58 shown in FIG. 15 constructed of suitable electrically conducting material, is mounted on cover plate pins 49 by press fitting it on the cover pins so that it is positioned between the cover plate 48 and the lower portion of the pivot switch 32 when the back plate is mounted on the casing. In the preferred embodiment of the invention the conductors are made of a conductive configuration of phosphor bronze or brass. The switch plate 58 is rectangular in shape with an extended spring finger 60. The extended spring finger 60 is bent so that its outer end engages the bulb contact 52.

The pivoted switch 32 is provided with a fulcrum hole 33 into which pivot pin 46 is placed allowing the pivoted switch to reciprocate between two set positons. The switch has extended flanged edges which are constructed to act as limit stops on each end of the recess 38 allowing the switch to be rotated between two limit positions but preventing the switch from moving in a full 360° rotation.

Figure 11:
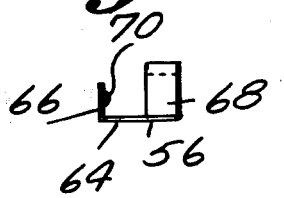
FIG. 11 is a side elevational view of the switch spring conductor of the light.
Figure 12:
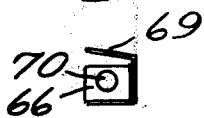
FIG. 12 is a front view of the switch spring conductor shown in FIG. 11.

A switch spring conductor 56, as seen in FIG. 11 is constructed with a base 64 and a perpendicular battery contact end 66. The battery contact end is provided with a dimple 70 for contact with the positive end of the battery 55. The switch spring 56 has a rectangular contact area 68 and arm 69. The switch spring conductor 56 sits with its base 64 beneath battery 55. The base 64 sits against the rear wall of the battery compartment with its battery dimple facing inwardly. The arm 69 has a rectangular surface which extends along the contact area and is constructed so that when the light is in its "on" position, as will be later described, its edge touches and is therefore in contact with the switch plate 58. That is to say, the spring is resilient with its normal tendency to be in the expanded position i.e. with its edge touching the conductor switch plate 58.

Figure 8:
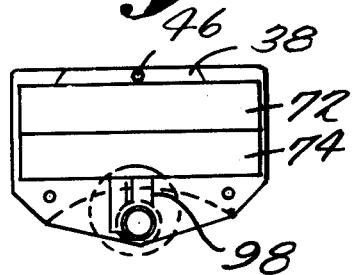
FIG. 8 is a rear elevational view of the casing of the light shown in FIG. 5.

The battery compartment 51 as is shown in FIGS. 7 and 8 consists of two battery holding areas 72 and 74. Battery holding area 72 is deeper with respect to battery holding area 74 with the dimension of both areas being such that they tightly enclose the two batteries.

Figure 10:
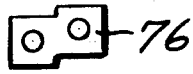
FIG. 10 is a plan view of the battery connector conductor of the light.

A dual positive-negative battery contact, 76, as seen in FIG. 10, is provided along the inner side of the battery compartment, opposite the side when the positive dimple 70 of contact spring 56 is provided. The dual contact is provided with two contact dimples to engage the negative end of battery 55 and positive end of battery 54.

The dual battery contact surface is made of any suitable conductive material to allow the electrical current to flow from one battery to another. As previously stated the preferred embodiment of the material is a phosphor bronze or brass composition.

Figure 13:
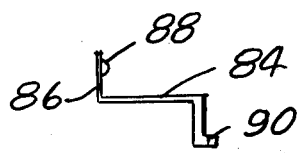
FIG. 13 is a side elevational view of the bulb connector conductor.
Figure 14:
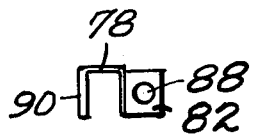
FIG. 14 is a front view of the bulb connector conductor shown in FIG. 13.

The bulb connector 82 as seen in FIGS. 13 and 14 connects the negative end of battery 54, seated in upper battery compartment 74, to the threaded side conductive surface 62 of the light bulb. The bulb connector 82 has a base 84 and a rectangular end 86 which is provided with a dimple contact 88. The base of the bulb connector has at one edge an L-shaped extension or finger 90. The L-shaped extension 90 connects the contact base 84 to the light bulb's side conductive surface 62. The extension 90 is frictionally held between the interior wall surface 92 of the boss and the light bulb threaded surface area 62 and sits in a recess 98 provided within the casing 22. The base 84 of bulb connector 82 sits between surface 100 of upper battery compartment 74 and battery 54.

As illustrated in FIG. 7 the light bulb 28 fits within the bore of boss 26 and is prevented from falling out of the front opening 27 of the boss light by shoulder 102, provided along the interior surface of the boss.

In operation, the light for vaginal speculum 20 is placed within a sanitary flexible transparent plastic bag 104. The light is then secured on the vaginal speculum 21 by placing the upper curvature 25 of the speculum in the space 45 formed between the curved wall 24, and the boss 26. This space and associated walls form a clip like structure holding the walls in place.

When a light is needed for illumination of the body cavity the wing of the pivoted switch 32, on the side opposite of the switch spring conductor 56 is depressed. The switch disengages the switch spring conductor so that the edge of the rectangular contact arm 69 of switch spring conductor 56 is placed in contact with the switch plate 58. This contact completes the electrical circuit and lights the bulb.

To turn the light off, it is only necessary to depress the wing of the pivoted switch on the same side as the switch spring conductor. Once depressed, the wing of the pivoted switch forces down and holds the rectangular contact arm of switch spring conductor 56 and thereby breaks the electrical circuit turning off the light.

If the light is desired for illumination of another examination area, the light is first removed from the plastic bag. The bag is then properly disposed of and the light then placed within another sanitary plastic bag. In this manner the light is not undly exosed to foreign germs or substances. The utilization of a new bag after each examination prevents germs or sources of infection from spreading from patient to patient.

While the preferred embodiment of the invention has been discussed it is understood that the invention is not limited to such an embodiment since it may be otherwise embodied in the scope of the appended claims.

What is claimed is:

1. A medical examination light able to be removably secured to a speculum of the type having a body and plurality of dilator members extending from said body, at least one said dilator members defining a curved rear wall, said light comprising light means adapted to mount directly to said curved rear wall of said dilator member of said speculum body, said light means comprising a housing, clip means defined by said housing allowing said housing to be securely yet moveably mounted to said curved upper wall of said upper dilator member, said clip means comprising a cylindrical boss protruding substantially perpendicular from said housing and a curved end wall defined by said housing spaced from said cylindrical boss a distance allowing the housing to be securely yet moveably placed on said speculum body, a light source mounted on said clip means and a source of power contained within said housing adapted to selectively energize said light source through switch means mounted on said housing.

2. A light as claimed in claim 1 wherein said light means is moveably mounted on the curved wall of the upper dilator member of said speculum body so that illumination will be provided between said dilator members, said illumination being provided by a light bulb mounted in said cylindrical boss which is positioned to direct light rays between said dilator members, said illumination traveling along the longitudinal axis of said boss and being able to illuminate a substantial amount of area proximate to said longitudinal axis when said housing is moved about said curved upper wall, said source of power comprising batteries and said switch means electrically connecting said power source to said light bulb for selectively energizing said light bulb.

3. A light housing as claimed in claim 1 wherein the outer wall of said boss and the curved end wall define a space having a radius of curvature less than the curved wall of said dilator member, said boss being substantially aligned with said dilator member yet able to move out of its original alignment in order to illuminate a larger area, said boss and curved end wall being adapted to frictionally engage and be removably mounted on said dilator member so that the axis of said boss extends between the dilator members of said speculum.

4. A lighted vaginal speculum comprising in combination a speculum comprising a body, a first elongated dilator arm member pivotally and movably mounted to said body and a second stationary dilator arm member also mounted to said body, the two members being adapted to dilate a body orifice, light means adapted to be removably mounted to said first dilator arm member, a flexible transparent covering enclosing said light means, said light means comprising a casing, defining a recessed area with an arcuate shaped wall and a cylindrical boss extending substantially perpendicular from said recessed area adjacent to said arcuate shaped wall, a light source mounted in said cylindrical boss extending from said casing and positioned thereon to project a light along the longitudinal axis of said first dilator arm to illuminate a dilator body orifice, battery means mounted to said casing and switch means moveably mounted on said casing to selectively energize said light source from said battery means.

5. A light instrument for use on a vaginal speculum of the type having a body and a plurality of dilator members extending from said body with at least one of the dilator members being provided with a curved rear wall, said instrument comprising a casing, said casing defining a base with a recessed area bounded by an arcuate wall and a cylindrical boss extending substantially perpendicular above said recessed area adjacent said wall, the distance between the arcuate wall of said casing bounding said recessed area and the outer wall of said cylindrical boss being not greater than the thickness of the curved rear of said dilator member of said speculum, a bulb mounted in said cylindrical boss, and a power source mounted within said casing and electrically connected to said bulb by switch means mounted to said casing.

* * * * *